United States Patent [19]
Vincent

[11] Patent Number: 5,183,007
[45] Date of Patent: Feb. 2, 1993

[54] MOTORCYCLE SAFETY HARNESS

[76] Inventor: John Vincent, 106 15th Ave. NE., Minot, N. Dak. 58701

[21] Appl. No.: 524,171

[22] Filed: May 15, 1990

[51] Int. Cl.[5] .......................... A62B 35/00; B62J 23/00
[52] U.S. Cl. ......................................... 119/96; 224/160
[58] Field of Search .............. 119/96; 182/3; 224/159, 224/160

[56] References Cited

U.S. PATENT DOCUMENTS

| | | | |
|---|---|---|---|
| 1,316,163 | 9/1919 | Kennedy | 119/96 |
| 2,108,566 | 2/1938 | Sanders | 119/96 |
| 2,132,556 | 10/1938 | Blackshaw | 119/96 |
| 2,574,178 | 11/1951 | Haller | 119/96 |
| 2,643,803 | 6/1953 | Bates | 119/96 |
| 2,699,284 | 1/1955 | Rose | 119/96 |
| 3,053,230 | 9/1962 | Klickstein et al. | 119/96 |
| 3,088,438 | 5/1963 | Oliphant | 119/96 |
| 4,273,215 | 6/1981 | Leggett | 182/3 |
| 4,324,205 | 4/1982 | Goldmacher | 119/96 |
| 4,560,097 | 12/1985 | Reynolds et al. | 224/160 |
| 4,746,084 | 5/1988 | Strong | 224/159 |
| 4,854,607 | 8/1989 | Mandracchim et al. | 119/96 |
| 4,911,105 | 3/1990 | Hocum | 119/96 |
| 4,915,277 | 4/1990 | Larreategui | 224/159 |

FOREIGN PATENT DOCUMENTS 4192 of 1915 United Kingdom ................ 224/159

Primary Examiner—Paul J. Hirsch
Attorney, Agent, or Firm—Kinney & Lange

[57] ABSTRACT

Disclosed is a harness for securing a child to an adult for safe riding of a motorcyle, the harness includes a belt portion which extends around both the adult and child and a harness portion attached to such belt and extending over the shoulders and around the waist of the child.

5 Claims, 4 Drawing Sheets

MOTORCYCLE SAFETY HARNESS

FIELD OF THE INVENTION

The present invention relates to harness straps and more particularly to a harness for securing a child to an adult for riding of a motorcycle.

BACKGROUND OF THE INVENTION

Harnesses have been created for a wide variety of purposes extending from the harnessing of a horse to a wagon to harness structures used in carrying a baby. Many of the harnesses previously developed have been used for safety purposes. Illustrative of such devices are the harnesses used in traversing rock ledges and those used during washing of widows of skyscrapers. Each use situation has its own peculiarities and needs. There is perhaps no situation where the need for safety is more critical than where a young child is riding on a motorcycle with an adult.

It is not uncommon for a parent to take a child on a motorcycle without a harness, for example, with the child grasping the belt of the adult. Accidents and death have occurred where the motorcycle strikes a pot-hole, the child bounces and loses his grasp of the adult's belt.

The present invention overcomes such risk by providing a harness which securely and reliably attaches the child to the adult. Moreover, the invention provides a harness which is readily attached to the child and the adult.

SUMMARY OF THE INVENTION

The present invention includes a first harness portion which is a belt that extends around the combined waists of the child and the adult. The present harness includes a second portion which encloses the upper body portion of the child and is secured to the combined belt. The upper body portion may include a belt portion which extends around the waist of the child and a pair of straps that extend from the child belt portion on the rear side of the child, over the shoulders, and is secured to the child belt portion in front of the child. The upper body harness portion may further include a cross-member to assure that the straps do not become dislodged and moved outwardly and downwardly over the shoulders and arms of the child.

IN THE DRAWINGS

DETAILED DESCRIPTION OF THE INVENTION

Figure 1:
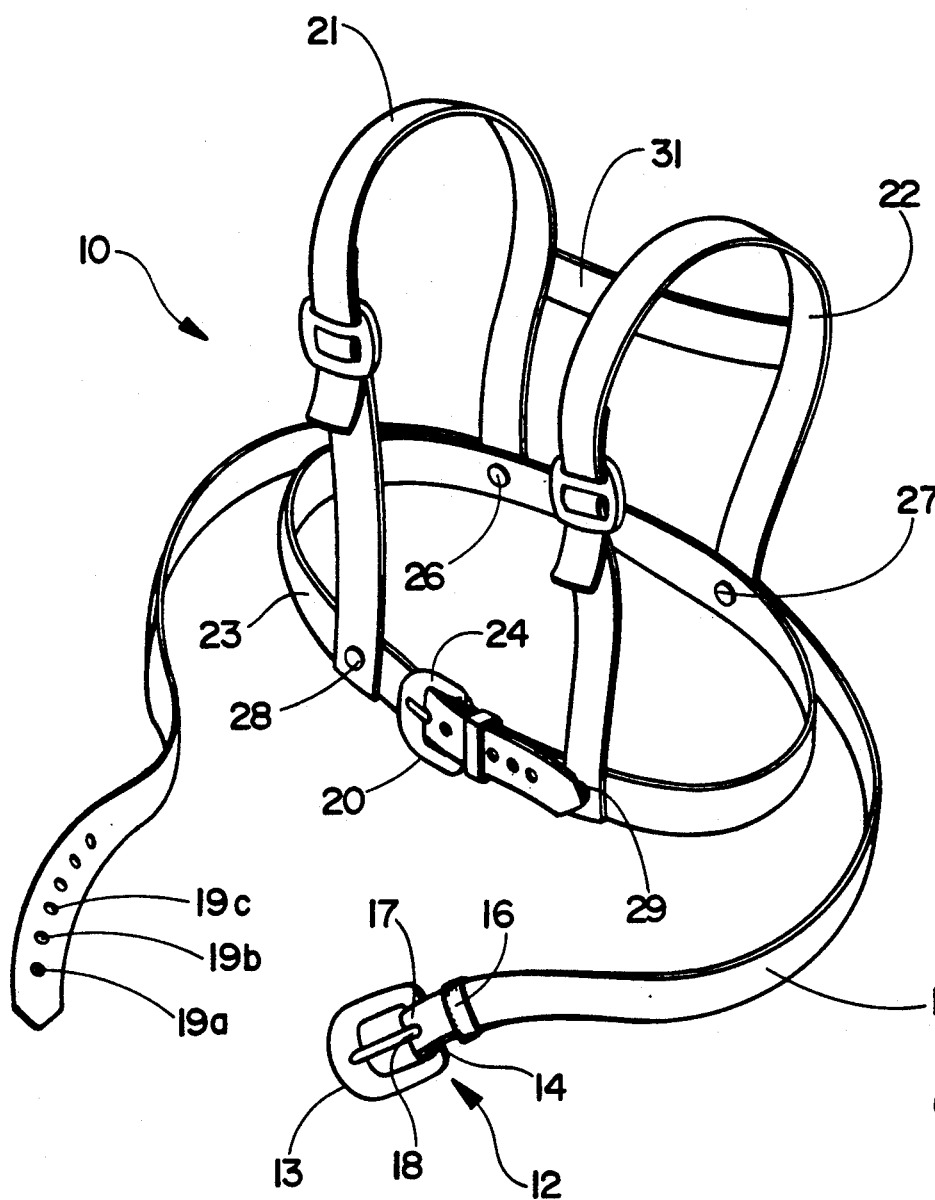
FIG. 1 shows a perspective view of the harness of the present invention.

The harness 10 of the present invention as illustrated in FIG. 1 includes a combined belt portion 11 which may be made for example of nylon or leather strap material. The strap material should be selected of a size and durability to assure that it will not break during use and will withstand substantial shock. The belt 11 includes a fastening device or buckle 12. The buckle 12 may be conventional in nature. For example, including a U-shaped metal portion 13, a cross bar 14, and a tongue 16. A loop portion 17 of belt 11 is secured around the cross member 14. The tongue 16 extends through a small opening 18 in loop 17. The tongue extends to engage the U-shaped portion 13. The other end of the belt may include a plurality of spaced openings such as 19a, 19b, and 19c for coaction with the tongue 14.

The upper body portion 20 may be constructed of nylon or leather strap material of a size somewhat smaller than the belt 11. The upper body portion 20 includes a pair of straps 21,22 which are secured to a small child belt 23. The belt 23 may include a suitable buckle 24 for purposes of securing the belt 23 around the waist of the child. The harness straps 21,22 are secured at the rear to the belt 11 such as by rivets 26,27 respectively. The straps 22,23 are connected at their forward ends to the belt such as by rivets 28,29 respectively. The upper body harness 12 may include a cross strap 31 which limits the spreading movement of the straps 21,22.

USE OF THE INVENTION

While the use and operation of the harness 10 is apparent from the aforedescription, it will be further described in order to assure a complete understanding of the invention. Prior to mounting of the motorcycle, the harness is placed on the child by extending the child's arms through the loops provided by straps 21,22 and securing the belt 23 around the waist of the child. This permits the combined belt 11 to hang from the upper body harness 20. The adult may set the child on the motorcycle and then mount the motorcycle. The child can then grasp the dangling portions of the belt 11 handing such portions to the adult. The adult then secures the combined belt around the adult's waist securing the buckle to the other end of the belt.

While a preferred embodiment of the present invention has been disclosed, it is to be recognized that various modifications may be made without departing from the broader scope of the present invention. The harness, for example, may be used by two adults rather than a child and an adult. Various other materials may be used in the construction of the harness such as a polymer strap material, a variety of other fastening devices for securing the harness portions together, as well as use of a wide variety of other types of buckles.

ALTERNATE EMBODIMENT

Figure 2:
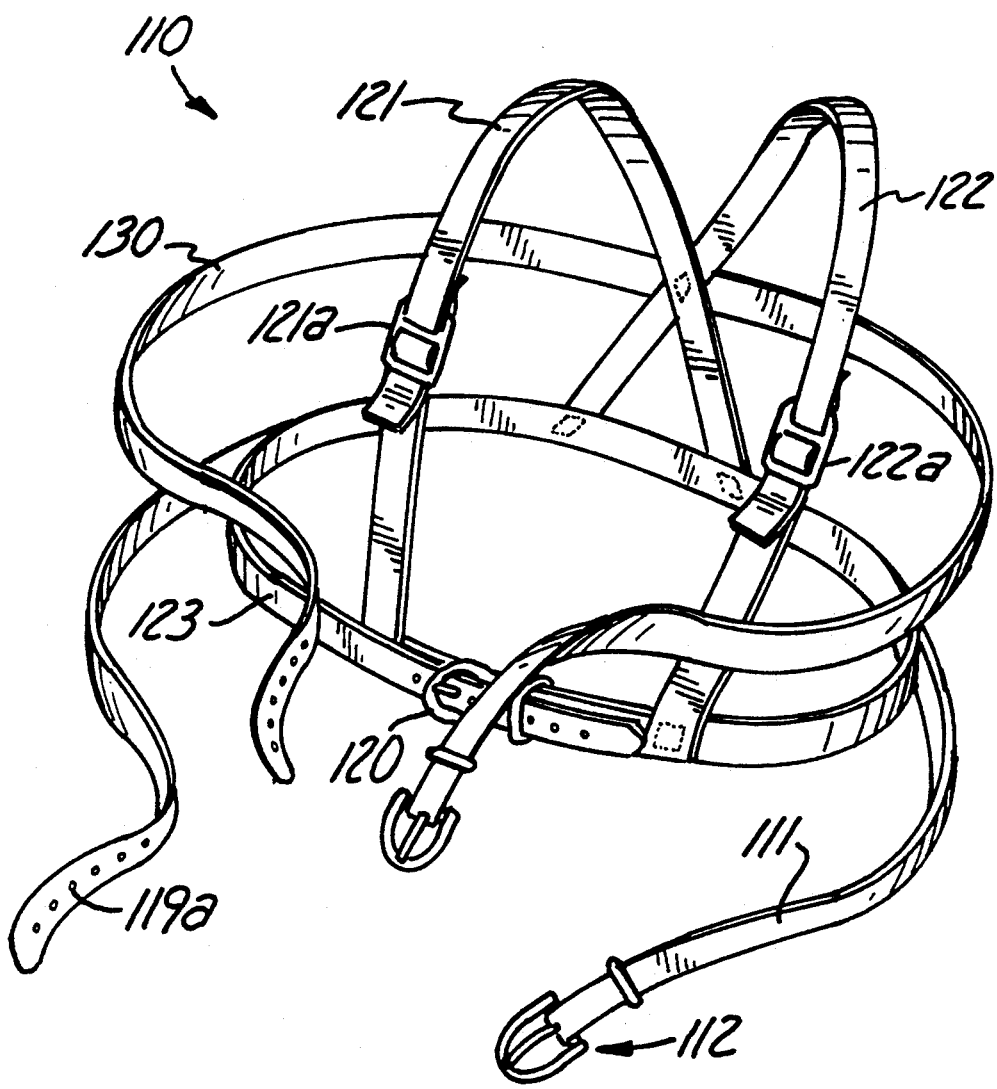
FIG. 2 shows a perspective view of an alternate embodiment of the present invention.

An alternate embodiment 110 is illustrated in FIG. 2. Harness 110 includes first belt 123 for securement around the waist of a rider. A pair of shoulder straps 121,122 are secured at the rear to the belt 123. The straps 121,122 cross at the back side of the user and are secured such as by rivets, sewing or the like on the front portion of the belt 123. Suitable size adjusting buckles 121a, 122a may be provided. A combined belt 111 is secured to the rear portion of the belt 123 and may include a suitable fastening mechanism such as buckle 112 and cooperating openings 119 in the belt 111. A secondary belt 130 is mounted to the upper portion of the rider's shoulder straps 121,122. The belt 130 wraps around the upper torso portion of both the rider and the driver, thus assuring that alignment of the rider's body and driver's body is maintained. This is particularly advantageous when cornering with a motorcycle. The driver leans to the inside to facilitate cornering of the cycle. The natural inclination of the rider on the other hand is to lean outwardly. This is detrimental to good control of the motorcycle. The present strap 130 requires that the rider move his upper body torso along with that of the driver. The harness 110 may be constructed of any suitable strap material such as nylon, rayon, leather or polymeric material.

FURTHER ALTERNATE EMBODIMENTS

Figure 3:
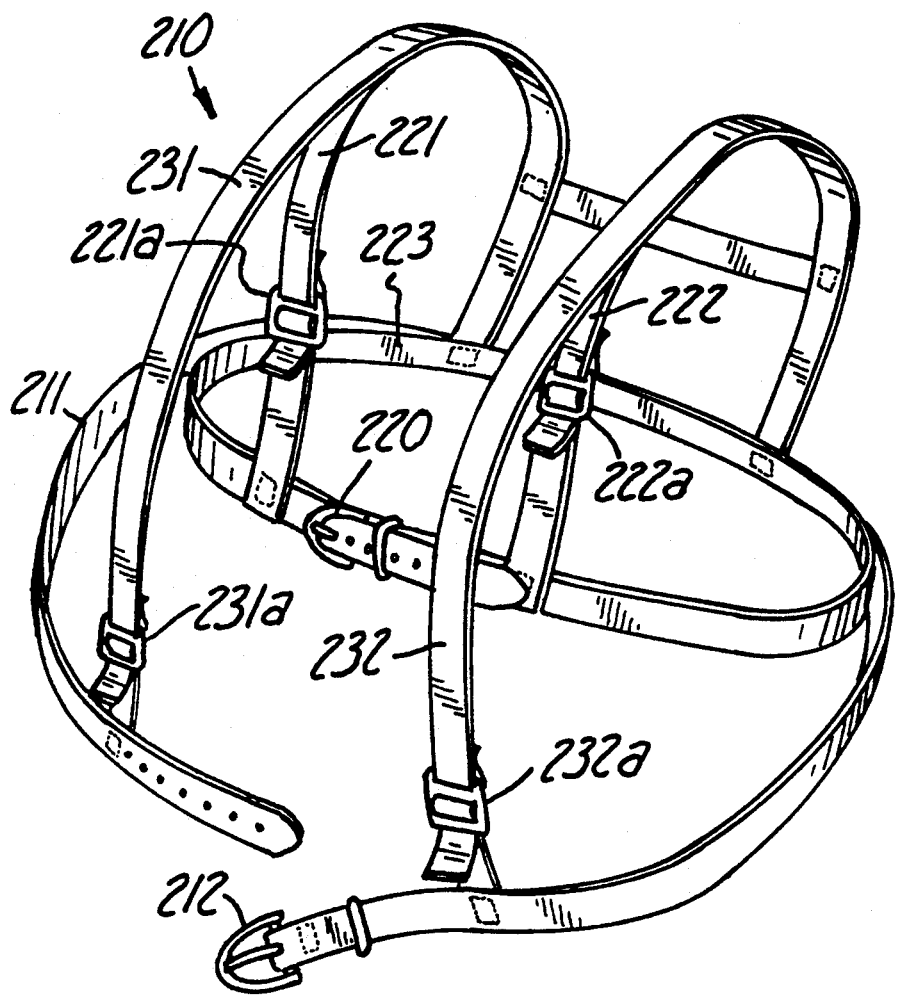
FIG. 3 shows another alternate embodiment of the present invention.

A further embodiment of the present invention is illustrated in FIG. 3. The harness 210 includes a rider belt 223 and a combined belt 211. Such belts may be suitably attached to each other adjacent the rear area such as by rivets, sewing and the like. The harness 210 includes a first pair of shoulder straps 221,222 which extend over the rider. The belt 223 may include a suitable fastener such as buckle 220. The shoulder straps 221,222 may include size adjustment buckles 221a,222a. A suitable cross member 231 may be secured between the straps 221,222. A second set of shoulder straps 231, 232 are attached at the rear side to the combined belt 211 and extend over the shoulders of both the rider and the driver. The straps 231,232 may include suitable size adjusting buckles 231a,232a. The forward ends are of course secured to the forward portion of the combined belt 211. The combined belt 211 may include a suitable fastening device such as buckle 212.

Figure 4:
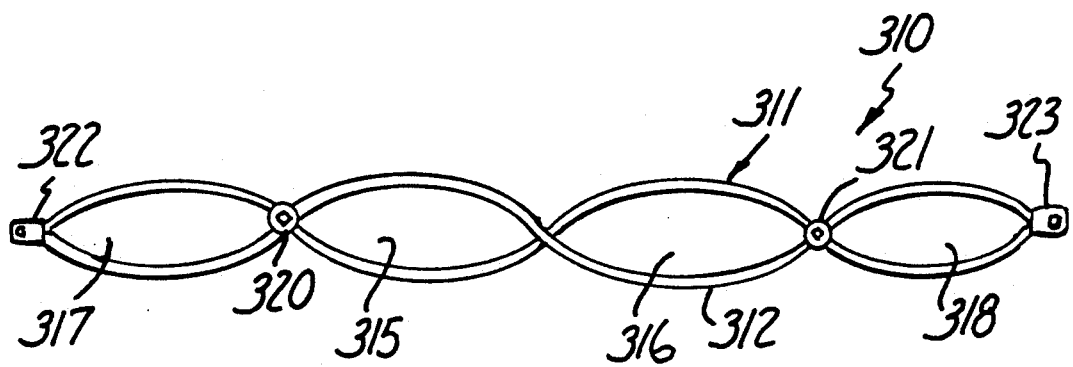
FIG. 4 shows a further alternate embodiment of the present invention.

Another alternate embodiment 310 is shown in FIG. 4. Harness 310 comprises a pair of belts 311,312 that are secured together in the form of a pair of figure eights. The rider's arms extend through the loops 315 and 316. The belts 311,312 cross in the area between the rider and the driver. The driver's arms extend through the loops 317,318. A pair of Velcro ® fastener patches 320,321 may be used to secure the belts at the point where they cross between the rider and driver. Another pair of Velcro ® patches 322,323 may be used to secure the belts 311,312 in front of the driver.

Various other modifications may be made as desired. What is claimed is:

1. A motorcycle safety harness for use by a child riding with an adult, said harness comprising:
    a first harness portion which comprises a first unitary belt having a length sufficient to extend around the combined waists of the child and the adult and having a single fastener positioned at a forward side of the adult, opposite from the child; and
    a second harness portion which encloses the upper body portion of the child and comprises a second belt which is secured around only the waist of the child and a pair of straps that extend from the second belt on the rear side of the child, over the shoulders of the child to the second belt on the forward side of the child, said second harness portion being secured to said first belt.

2. The harness of claim 1 wherein said second harness portion further includes a cross-member connected between the pair of straps to assure that the straps do not become dislodged and move outwardly and downwardly over the shoulders and arms of the child.

3. A motorcycle safety harness for use by a driving person and a riding person, said harness comprising:
    a first belt that extends around the waist of the riding person;
    a second unitary belt that is secured to said first belt and is adapted to enclose the combined waists of the riding person and the driving person;
    a first upper body harness portion which encloses the upper body portion of the riding person and is secured to the first belt, said first upper body harness portion comprising a first pair of straps that extend from the first belt on the rear side of the riding person to the first belt on the forward side of the riding person; and
    a second upper body harness portion comprising a second pair of straps extending from the second belt at the rear side of the riding person, over the shoulders of the riding person and the driving person and secured to the second belt at the forward side of the driving person.

4. The harness of claim 3 wherein said harness further includes a third belt that extends around the combined upper torso portions of the riding person and the driving person and is mounted to the first pair of straps.

5. A motorcycle safety harness for use by a riding person and a driving person, the harness comprising at least one unitary belt extending around both the torso of the riding person and the torso of the driving person to maintain vehicle upper body alignment of the riding person and the driving person, the at least one unitary belt comprising first and second unitary belts secured together in the form of a pair of figure eights to create a pair of inner loops and a pair of outer loops, the first and second belts extending around the rear side of the riding person, crossing between the riding person and the driving person and extending around the forward side of the driving person such that the riding person's arms extend through the inner loops and the driving person's arms extend through the outer loops.

* * * * *